(12) United States Patent
Ruppert et al.

(10) Patent No.: US 8,075,905 B2
(45) Date of Patent: Dec. 13, 2011

(54) DENTAL MATERIALS EQUIPPED WITH ACTIVE ANTI-PLAQUE SUBSTANCE(S)

(75) Inventors: Klaus Ruppert, Maintal (DE);
Karl-Heinz Renz, Frankfurt (DE);
Sebastian Vogt, Erfurt (DE)

(73) Assignee: Heraeus Kulzer GmbH, Hanau (DE)

( * ) Notice: Subject to any disclaimer, the term of this patent is extended or adjusted under 35 U.S.C. 154(b) by 267 days.

(21) Appl. No.: 12/429,353

(22) Filed: Apr. 24, 2009

(65) Prior Publication Data

US 2009/0297458 A1 Dec. 3, 2009

(30) Foreign Application Priority Data

Apr. 29, 2008 (DE) .......................... 10 2008 021 473

(51) Int. Cl.
*A61F 13/00* (2006.01)
*A61K 7/16* (2006.01)

(52) U.S. Cl. ........ 424/422; 424/443; 424/440; 424/464; 424/478; 424/468; 424/457

(58) Field of Classification Search .................... 424/49, 424/422, 443, 440
See application file for complete search history.

(56) References Cited

U.S. PATENT DOCUMENTS

| | | | |
|---|---|---|---|
| 4,206,215 A | | 6/1980 | Bailey |
| 5,472,712 A * | | 12/1995 | Oshlack et al. ............... 424/480 |
| 5,580,578 A * | | 12/1996 | Oshlack et al. ............... 424/468 |
| 5,639,476 A * | | 6/1997 | Oshlack et al. ............... 424/468 |
| 6,143,353 A * | | 11/2000 | Oshlack et al. ............... 427/2.21 |
| 6,395,303 B1 * | | 5/2002 | Staniforth et al. ............ 424/499 |
| 6,780,504 B2 * | | 8/2004 | Rupprecht et al. ............ 428/354 |
| 6,866,867 B2 * | | 3/2005 | Staniforth et al. ............ 424/499 |
| 7,790,215 B2 * | | 9/2010 | Sackler et al. ............... 427/2.21 |
| 2002/0142036 A1 * | | 10/2002 | Rupprecht et al. ............ 424/484 |
| 2002/0182259 A1 * | | 12/2002 | Staniforth et al. ............ 424/499 |
| 2003/0190362 A1 * | | 10/2003 | Sackler et al. ................ 424/478 |
| 2005/0048005 A1 | | 3/2005 | Stockel |
| 2005/0147673 A1 * | | 7/2005 | Staniforth et al. ............ 424/464 |
| 2005/0281757 A1 * | | 12/2005 | Ibrahim et al. ................. 424/49 |
| 2006/0193877 A1 * | | 8/2006 | Tengler et al. ............... 424/400 |
| 2006/0205838 A1 | | 9/2006 | Velamakanni et al. |
| 2006/0243297 A1 * | | 11/2006 | Brown .......................... 132/321 |
| 2007/0053848 A1 | | 3/2007 | Stockel |
| 2007/0071796 A1 * | | 3/2007 | Bartholomaus ............... 424/443 |
| 2007/0092553 A1 * | | 4/2007 | Tengler et al. ............... 424/440 |
| 2008/0286342 A1 * | | 11/2008 | Bartholomaus et al. ....... 424/443 |
| 2009/0297458 A1 * | | 12/2009 | Ruppert et al. ................. 424/49 |

FOREIGN PATENT DOCUMENTS

| | | |
|---|---|---|
| DE | 37 03 080 | 1/1988 |
| DE | 37 03 120 | 1/1988 |
| DE | 19937093 | 2/2001 |
| DE | 10332680 | 2/2005 |
| DE | 102007040569 | 3/2009 |
| DE | 102009004368 A1 * | 7/2010 |

* cited by examiner

*Primary Examiner* — Robert J Hill, Jr.
*Assistant Examiner* — Peter A Salamon
(74) *Attorney, Agent, or Firm* — Norris McLaughlin & Marcus P.A.

(57) ABSTRACT

A process by means of which the colonization by plaque on dental materials can be permanently prevented or delayed without the product properties of the dental material being negatively influenced. The process involves equipping the dental material with anti-plaque substance, namely at least one molecularly dispersely distributed octenidine salt or dequalinium salt. Also disclosed is a dental material so equipped.

17 Claims, 1 Drawing Sheet

DENTAL MATERIALS EQUIPPED WITH ACTIVE ANTI-PLAQUE SUBSTANCE(S)

The invention relates to dental materials equipped with active anti-plaque substance(s).

BACKGROUND

Polymeric dental materials, in particular those based on acrylate/methacrylate, which are introduced into the oral cavity to remain there permanently tend to become colonised by plaque on the material surface in the case of lack of oral hygiene.

Plaque is composed of various bacteria which become anchored firmly to surfaces such as e.g. teeth or dental materials by proteins and carbohydrates. Further bacteria can then settle on this first bacteria layer thus forming a three-dimensional colony. As a result of certain substances released by the bacteria, this "biofilm" is almost immune to attack by antibiotics.

Apart from the hygiene aspect, plaque leads, in the advanced stage, also to strong discolouration resulting in aesthetically adverse effects.

STATE OF THE ART

A reduction of plaque colonisation can be effected either by biocides or by a hydrophobic coating on the dental material preventing the adhesion of the bacteria on the material.

The use of quaternary ammonium salts as antimicrobial additives has been known for a long time. Thus silane with quaternary ammonium groups as functional group is made by Microbeshield, for example, and is marketed for antibacterial finishing of filters, textiles and wound substrates. Moreover, silver-containing types of glass, salts or zeolites have been proposed as antimicrobial additives.

TASK IN HAND

It is the purpose of the present invention to provide a process by means of which the colonisation by plaque on dental materials can be permanently prevented or delayed without the product properties of the dental material being negatively influenced.

In this respect, the following core requirements are of importance:
- A homogeneous distribution of the active substances within the interior of the material (bulk) and on the material surface should be guaranteed, i.e. conversely: a spot-type distribution must be avoided.
- The material must not exhibit any micro-pores and macro-pores following the release of the active substance (aesthetics, cracking, starting point and new colonisation).
- The inactivation of the active substance on the surface should be made difficult by subsequent diffusion from the interior (bulk).
- A wide spectrum of effectiveness against typical oral germs should be the aim.
- The active substance should be released in a delayed manner.
- The active substance should have such a high rate of release that an antimicrobial effectiveness arises while no toxic or irritating/sensitising effects occur.
- The active substance must not interfere with the polymerisation of the product or have a negative effect on the properties of the material; in particular, no phase separation (plasticizer effect) must occur.
- Only a low probability resistance formation of the typical oral germs vis-à-vis the active substance ought to arise.

Octenidine, its manufacture and its anti-plaque effect are known as such (Merck Index 14th ed. 2006, Monograph number: 0006754). The compound is used predominantly in mouth rinses. In U.S. Pat. No. 4,206,215, it is also recommended to use the antimicrobial active substances described therein in varnishes or coatings.

INVENTION

According to the invention, dental material equipped with active anti-plaque substance is proposed as described hereinbelow which material contains at least one molecularly dispersely distributed octenidine salt or dequalinium salt. Further preferred embodiments are indicated in the dependent claims. The invention also relates to a process for equipping a dental material with anti-plaque properties and to a method of using octenidine salt or dequalium salt to equip a dental material with anti-plaque properties.

BRIEF DESCRIPTION OF THE DRAWING

The invention will be described with reference to the drawing, wherein.

Figure 1:
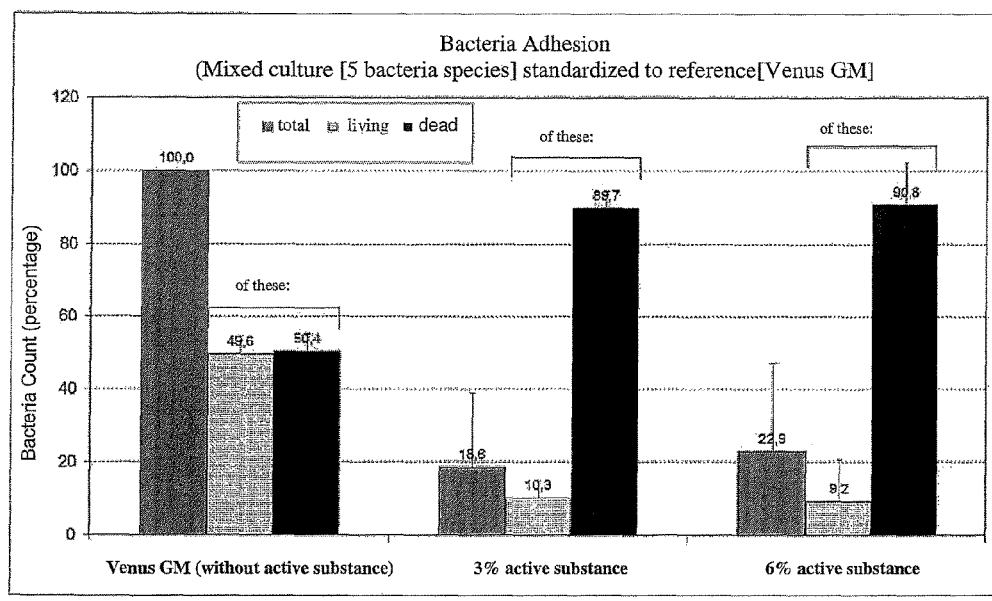
FIG. 1 is a graph depicting the quantity of adhering bacteria as a function of the quantity of active substance.

In this case, octenidine salt should be understood to be a compound with the basic dicationic bipyridinium structure according to CAS No. 70775-75-6. This should include also slight modifications to the basic chemical structure, e.g. with a variation of the central alkyl chain (n=7-13), a variation of the terminal alkyl chains (n=4-12), and a variation of the anions. Instead of the octenidine salt, dequalinium salts with a similar structure can be involved.

Suitable anions of such salts are, apart from the usual inorganic anions chloride, sulphate and phosphate, also "organic anions" (e.g. fatty acid anions, carboxylic acid anions, alkyl sulphonic acids and aryl sulphonic acids, alkyl sulphates and aryl sulphates). They are not free radical polymerisable. Examples of these are hexanoates, dodecylates, stearates and dodecyl sulphates.

Such octenidine salts exhibit a certain mobility/migratability in the dental material.

Free radical polymerisable anions of unsaturated fatty acids (e.g. oleates, sorbates) can also be used. During hardening of the dental material, these can be incorporated by polymerisation and are immobile, whereas the cationic portion can be mobilised. A combination of salts with anions of both groups is also possible. In this way, the release, via migration, of the salts or the cations from the dental material is possible at different rates. Finally, a release of residual substance is possible as a result of the abrasion of the material.

Dental materials equipped with active anti-plaque substance according to the invention consist e.g. of filling composites, mixed composites, prosthesis materials, materials for artificial teeth, moulding compounds, protective varnishes, fissure sealants, cements, adhesives or dentin bondings. Veterinary materials such as hoof material are also suitable.

The octenidine salt or dequalinium salt is present in the dental material preferably in quantities of less than 10% by weight to 6% by weight. This means in particular that the release of active substance occurs in non-toxic, non-irritant and non-sensitising but antimicrobially effective quantities. In addition, the quantities should be chosen in such a way that the active substance is liberated in odour and taste neutral amounts. The possibility of discolouration of the dental material should also be excluded by the selection of the quantity. Octenidine salt and/or dequalinium salt is present in the dental material e.g. in quantities of between 1 and 6, preferably 3-6% by weight. However, quantities of or up to 1 or 2% by weight, depending on the migratability, may be sufficient.

For incorporation by polymerisation or homogeneous distribution in the dental material, the salt is appropriately added to the corresponding monomer or monomer mixture. Examples of suitable monomers are those common in the dental sector such as e.g. monomeric (meth)acrylates such as ethylene glycol dimethacrylate EDMA, diethylene glycol dimethacrylate, triethylene glycol dimethacrylate TEGDMA, glycerol dimethacrylate GDMA, glycerol trimethacrylate, trimethylol propane trimethacrylate, pentaerythritol dimethacrylate, pentaerythritol trimethacrylate, pentaerythritol tetramethacrylate, derivatives of bisphenol A such as bisphenol A dimethacrylate and bisphenol A diglycol dimethacrylate, urethane methacrylate obtainable from diisocyanates and hydroxyalkyl methacrylates as well as reaction products of polyols, diisocyanates and hydroxyalkyl methacrylates according to DE 37 03 080 A1 or DE 37 03 120 A1; $C_{1-12}$ alkyl methacrylates, preferably $C_{1-4}$ alkyl methacrylates such as methyl methacrylate, ethyl methacrylate, n-propyl methacrylate, isopropyl methacrylate, n-butyl methacrylate and t-butyl methacrylate, hydroxyalkyl $C_{1-4}$ methacrylates such as 2-hydroxyethyl methacrylate, 2-hydroxypropyl methacrylate, diethylene glycol monomethacrylate, triethylene glycol monomethacrylate, alkoxy $C_{1-4}$ alkyl methacrylates such as 2-methoxyethyl methacrylate, 3-methoxybutyl methacrylate and ethyl triglycol methacrylate. Suitable monomers of these are, respectively, the monomers themselves, polymerisable prepolymers produced therefrom and mixtures thereof.

Suitable fillers are in particular quartz powder and glass ceramic powders, aluminium oxides and/or silicon oxides. These include the so-called microfillers whose grain size is in the nm range, such as highly disperse, finely particulate pyrogenic or precipitated silicic acid and the so-called macrofillers whose grain size is in the micrometer range, in particular granular silicic acid or ground types of dental glass. The types of glass are e.g. barium glass powder, barium silicate glass powder, lithium powder or aluminium silicate glass powder, preferably aluminium silicate glass which may be doped with barium, strontium or rare earths (compare DE-PS 24 58 380). Finely ground types of glass or quartz with mean particle sizes of between approximately 1 and 10 micrometers and highly disperse $SiO_2$ with mean particle sizes of between approximately 10 and 400 nm are preferred.

Depending on the type of polymerisation initiator used, curing of the dental compositions may take place by thermal, photochemical or redox-induced radical polymerisation.

Preferred examples of thermal initiators are the known peroxides such as e.g. dibenzoyl peroxide, dilauryl peroxide, tert-butyl peroctoate or tert-butyl perbenzoate and azobisisobutyroethyl ester, azobisisobutyronitrile, azobis-(2-methyl propionamidine)dihydrochloride, benzpinakol or 2,2-dimethyl benzpinakol.

Benzophenone, benzoine and their derivatives or alpha-diketones or their derivatives such as 9,10-phenanthrene quinone, diacetyl or 4,4-dichlorobenzyl are preferred photoinitiators. Camphor quinone and 2,2-dimethoxy-2-phenyl acetophenone are particularly preferred and alpha-diketones in combination with amines as reducing agents such as e.g. 4-(N,N-dimethylamino) benzoic acid ester, N,N-dimethyl aminoethyl methacrylate, N,N-dimethyl-sym.-xylidine or triethanol amine are used particularly preferably. In addition, acyl phosphines such as e.g. 2,4,6-trimethyl benzoyl diphenyl- or bis(2,6-dichlorobenzoyl)-4-N-propylphenyl phosphine oxide are particularly suitable.

Redox initiator combinations such as e.g. combinations of benzoyl peroxide or lauryl peroxide with N,N-dimethyl-sym.-xylidine or N,N-dimethyl-p-toluidine are preferably used as initiators for polymerisation carried out at room temperature.

The following examples illustrate the invention in further detail. Information concerning parts and percentages relate here and in the remaining description to the weight, unless indicated otherwise.

PRACTICAL EXAMPLES

Production of a Dental Composite with Homogeneously Molecularly Dispersely Distributed Octenidine Dihydrochloride Octenidine dihydrochloride is dissolved in such a quantity of bis-GMA with slight heating that the end concentration of octenidine dihydrochloride in the composite is 3 to 6% by weight.

The addition of TEGDMA as reactive thinner, usual photoinitiators and stabilisers as well as 65% by weight of dental glass in a grain size of ~1 μm and, for adjusting the rheology, approx. 8% by weight of pyrogenic silicic acid Aerosil OX50 completes the filling composite. If necessary, colour pigments are added for colour adjustment.

Production of a Dental Composite with Homogeneously Molecularly Dispersely Distributed Octenidine Dilactate Octenidine dilactate is added to a mixture of EDMA, TEGDMA and an aliphatic dimethacrylate in such an amount that the end concentration of octenidine dilactate amounts to 3 to 6% by weight. Stirring is carried out with slight heating in order to completely dissolve the octenidine dilactate.

The addition of common photoinitiators and stabilisers, 45% by weight of prepolymers based on silicic acid and, in order to adjust the rheology, approx. 30% by weight of silicic acids of different types completes the composite. If necessary, colour pigments are added for colour adjustment.

Production of Octenidine Dilactate 100 ml of methanol are placed into a round-bottomed flask. Following the addition of the corresponding molar quantity of octenidine dihydrochloride, stirring is carried out for 10 mins and a stoichiometric quantity of silver lactate is added. Boiling is carried out for approx. 60 mins under reflux, the residue is then filtered off and the solvent is drawn off.

Hardening to Form Test Specimens

The composite Venus® (Heraeus Kulzer) to which the antimicrobial additive has been added is processed to form test panels with a diameter of 20 mm and a thickness of 1 mm by spreading it into a steel mould. On exposure to the light of the dentist lamp Translux Energy® (Heraeus Kulzer) in line with the specifications contained in ISO4049, the test specimens is cured.

The dental material may further have an antimicrobial component and/or an additional component selected from the group consisting of monocationic antiseptics, dicationic antiseptics, oligomeric or polymeric cationic antiseptics and antiseptic heavy metal compounds.

Test of the Antimicrobial Effect

The following sterile specimens were placed into flow chambers:
  Venus® reference material without active substance,
  Venus® with 3% active substance,
  Venus® with 6% active substance,
  1× titanium (control).

Subsequently, the flow chambers were connected to a bioreactor which contained a freshly prepared bacterial mixed culture (*Streptococcus mutans, Streptococcus sanguinis, Actinomyces viscosus, Fusobacterium nucleatum, Veillonella parvula*) in the logarithmic growth phase with defined proportions of the individual bacteria species for the execution of the plaque adherence tests. The incubation of the mixed culture took place in line with a continuous culture management anaerobically at 37° C., pH=7.2 and 5.0 g/l sucrose as source of C. By means of hose pumps, the bacterial mixed culture was passed through the flow chambers over the material surface. Testing of the biofilm formation took place over a period of 5 days. After removing the specimens from the flow chambers, rinsing of the specimens was carried to remove non-adhering bacteria.

Analyses:

The analysis of the bacteria adhesion on the specimen surfaces was carried out following selective fluorescence staining of adhering living and dead microorganisms.

Results:

The addition of the active substance has a marked effect on the quantity of adhering bacteria and in particular on the vitality of the adhering bacteria population. FIG. 1 shows the adhesion of plaque bacteria (mixed culture, 5 species) after 5 days of dynamic cultivation (flow chamber) on polymer materials (composite Venus®, Heraeus Kulzer) with and without active substance. A reduction of the bacteria count by approximately 80% was observed.

The non-modified polymer material exhibits a distribution of living and dead bacteria of approximately 50:50 (compare FIG. 1). As a result of the addition of active substance, the ratio is markedly displaced in the direction of dead bacteria (10% living, 90% dead). This is clear proof of the antibacterial effectiveness of the additive used.

What is claimed:

1. Dental material equipped with active anti-plaque substance, said dental material comprising at least one molecularly dispersely distributed octenidine salt or dequalinium salt, wherein
   the salt is present in a dissolved form molecularly dispersed in one or several (meth)acrylate based dental monomers;
   the salt has at least one anion from the group consisting of chloride, sulphate, phosphate, fatty acid anions, carboxylic acid anions, alkyl sulphonic acids and aryl sulphonic acids, alkyl sulphates and aryl sulphates;
   the material comprises at least one polymerization initiator.

2. Dental material according to claim 1, further comprising at least one substance selected from the group consisting of polymerization stabilisers and fillers.

3. Dental material according to claim 1, wherein the salt is temperature stable up to an upper limit of 100° C.

4. Dental material according to claim 1, wherein the salt comprises at least one non free radical polymerizable anion.

5. Dental material according to claim 1, wherein the salt is capable of migration in the dental material within a temperature range of 15-40° C.

6. Dental material according to claim 1, which comprises the salt having free radical polymerizable anion.

7. Dental material according to claim 6, which additionally comprises at least one octenidine salt or dequalinium salt having a non free radical polymerizable anion.

8. Dental material according to claim 6, which comprises anions incorporated by polymerization.

9. Dental material according to claim 1, wherein the total quantity of octenidine salt and/or dequalinium salt amounts to <10% by weight of the dental material.

10. Dental material according to claim 1, which further comprises an antimicrobial component.

11. Dental material according to claim 10, which further comprises a component selected from the group consisting of monocationic antiseptics, dicationic antiseptics, oligomeric or polymeric cationic antiseptics and antiseptic heavy metal compounds.

12. Dental material according to claim 1, wherein the polymerization initiator is selected from the group consisting of at least one thermal initiator, at least one photoinitiator and at least one redox initiator.

13. Dental material according to claim 1, wherein the dental material is cured.

14. Process for equipping dental material based on (meth-)acrylate with anti-plaque properties, said process comprising distributing at least one octenidine salt or dequalinium salt in a dissolved form and molecularly dispersed manner in one or several a (meth-)acrylate monomers before polymerizing the one or several monomers, the salt has at least one anion from the group consisting of chloride, sulphate, phosphate, fatty acid anions, carboxylic acid anions, alkyl sulphonic acids and aryl sulphonic acids, alkyl sulphates and aryl sulphates, and adding at least one polymerization initiator to the monomer.

15. Process according to claim 14, wherein the polymerization initiator is selected from the group consisting of at least one thermal initiator, at least one photoinitiator and at least one redox initiator.

16. Process according to claim 14, further comprising curing the dental material.

17. Dental material according to claim 1, equipped with active anti-plaque substance, said dental material comprising at least one molecularly dispersely distributed octenidine salt or dequalinium salt, wherein the dental material is selected from the group consisting of filling composites, mixed composites, prosthesis materials, materials for artificial teeth, moulding compounds, protective varnishes, fissure sealants, cements, adhesives and dentin bondings.

* * * * *